US00PP09100P

United States Patent [19]

van Andel

[11] Patent Number: Plant 9,100

[45] Date of Patent: Apr. 4, 1995

[54] ALSTROEMERIA PLANT NAMED STAMOND

[75] Inventor: Jacob van Andel, Aalsmeer, Netherlands

[73] Assignee: Van Staaveren B.V., Netherlands

[21] Appl. No.: 201,564

[22] Filed: Feb. 25, 1994

[51] Int. Cl.[6] ..... A01H 5/00

[52] U.S. Cl. ..... Plt./87.1

[58] Field of Search ..... Plt. 87.1

*Primary Examiner*—James R. Feyrer

*Attorney, Agent, or Firm*—Christie, Parker & Hale

[57] ABSTRACT

A new and distinct Alstroemeria variety producing flowers of good quality having inner petals with greyed purple spots against a primarily white background with a central section with yellow intonation.

1 Drawing Sheet

BACKGROUND OF THE INVENTION

The present inventon relates to a new and distinct cultivar of Alstroemeria originated as a seedling by crossing as seed parent an unreleased seedling identified as 87r1345-1 and as pollen parent an unreleased seedling identified as 87G1069-2 among my collection of Alstroemeria seedlings maintained under controlled conditions in a greenhouse at Van Staaveren B.V., Aalsmeer, The Netherlands for developmental purposes. The varietal denomination of the new variety is 'Stamond'.

The first act of asexual reproduction of 'Stamond' was in Aalsmeer, The Netherlands by propagation by dividing rootstocks. Asexual reproduction through successive generations has demonstrated that the combination of characteristics as herein disclosed for 'Stamond' are firmly fixed and retained through successive generations of asexual reproduction.

'Stamond' has not been observed under all possible environmental conditions. Phenotypic expression may vary with variations in environment such as temperature, light intensity, day length and growing and cultural conditions.

SUMMARY OF THE INVENTION

Flowers of the new variety of Alstroemeria, 'Stamond', are of the butterfly type and are characterized by inner lateral petals having greyed purple spots against a primarily white background with a central section having yellow intonation, and some greenish veination at the apices of outer petals.

The plant produces numerous flowering stems, which is a desirable characteristic in a cut-flower variety. The flower-bearing stems are long, strong and of excellent quality. It has been established that 'Stamond' grows productively under greenhouse conditions. The variety is reproducible both by division of rhizomes and by tissue culture.

DESCRIPTION OF ILLUSTRATIONS

The new variety of Alstroemeria hybrid is illustrated in the accompanying illustration, which shows typical flower and foliage characteristics, with colors being as nearly true as is possible for illustrations of this type.

DETAILED DESCRIPTION OF THE NEW VARIETY

The following is a detailed description of the new cultivar of Alstroemeria hybrid as observed in a greenhouse in Aalsmeer, The Netherlands. Color designations indicated are in accordance with The Royal Horticultural Society Colour Chart by color plate designations.

Botanical classification:

*Family.*—Amaryllidaceae.

*Genus.*—Alstroemeria sp.

*Commercial.*—Alstroemeria hybrid.

Origin: Seedling.

PLANT

Form: Bush.

Shape: Upright.

Height: 150–250 cm.

Internode length: 1–8 cm.

Growth rate: Fast; the length of time (number of days) taken from young plants (i.e. rooted rootstocks, the stage of developement in which the varieties are sold) to flowering stage under commerical greenhouse conditions is 80–90 days.

Pinching required: No.

Main stem or cane length: About 200 cm.

Internode length: 1–8 cm.

Branching character: None.

Growth: Vigorous.

Strength: Strong.

Foliage:

*Quantity.*—Abundant.

*Number of leaves.*—35–45.

*Size of leaf.*—Length: 15–20 cm. Width: 3–5 cm.

*Shape of leaf.*—Elliptical.

*Margin type.*—Straight.

*Texture.*—Glossy.

*Color.*—Upper side: Near 137A. Underside: Near 137C.

*Rhizomes.*—Yes. Color: Near 155D. Size: 10–30 cm.

INFLORESCENCE — FLOWER/FLORET

Blooming habit: Continuous.

Are spent umbels required to be pinched to maintain the claimed plant in a continuous blooming condition? No.

Blooms: Profusely.

*Spring.*—Yes.

*Fall.*—Yes.

*Has tendency to give few blooms in fall.*—No.

Size: Very large.

*Diameter.*—About 7 cm.
*Depth.*—About 5 cm.
Stage of development: When first anthers release their pollen.
Borne: Singly.
Shape or form:
*When bloom first opens.*—Cup.
*When bloom matures.*—Cup.
Petalage:
*Number of petals.*—6.
*Arrangement.*—2 concetric circles of 3 petals.
*Form.*—Outer petals: Obovate, emarginate tips. Inner petals: Oblanciolate.
*Margin type.*—Minutely crimped.
*Apex.*—Pointed.
*How long do petals stay on stem?*—About 4 weeks.
*Texture.*—Soft.
*Apperance.*—Velvety.
*Color (summer/fall).*—Outer petal/floret: Body near 155D; base near 155D; reverse side near 62B/155D. Inner petal/floret: Body near 4C/155D; base near 155D; reverse side near 4C/155D. The two inner lateral petals have 20–40 spots, color near 185A; outer petals have about 1–2 central spots of the same color; the inner median petal has 0–15 spots, color near 185A.
Peduncle or flower stem:
*Length.*—5–8 cm.
*Color.*—Near 137B.
*Strength.*—Strong.
*Upright.*—Yes.
Discoloration after full bloom? No.
Is bloom affected by wet or hot weather? No.
Persistence (does flower hang on and dry?): No.
Diesease resistance: Unknown.
Fragrance: None.
Lasting quality:
*On plant.*—About 4 weeks.
*As cut flower.*—20–25 days.

BUD

Size:
*Diameter.*—1–2 cm.
*Depth or length.*—2–4 cm.
Form or shape: Pear-shaped.
*Long.*—Yes.
*Pointed.*—No.
Rate of opening: Fast.
Color of petals/florets:
*When sepals first divide.*—Near 155D.
*When petals begin to unfurl.*—Near 155D.
Peduncle or flower stem:
*Length.*—5–8 cm.
*Hairy.*—No.
*Strength or character.*—Erect.
*Color.*—Near 137B.

REPRODUCTIVE ORGANS

Stamen:
*Number.*—6.
*Arrangement.*—Side by side around the style.
Anthers:
*Size.*—8–10 mm.
*Color.*—Near 161A.
Filaments:
*Length.*—About 5 cm.
*Color.*—Near 62D to near 155D.
Pollen:
*Color.*—Near 161A.
Pistils:
*Number.*—1.
Styles:
*Length.*—4–5 cm.
*Color.*—Near 62D to near 155D.
Stigmas:
*Color.*—Near 155D.

FRUIT

Fertile: No.
Shape: Round.

I claim.

1. A new variety of Alstroemeria plant substantially as herein shown and described.

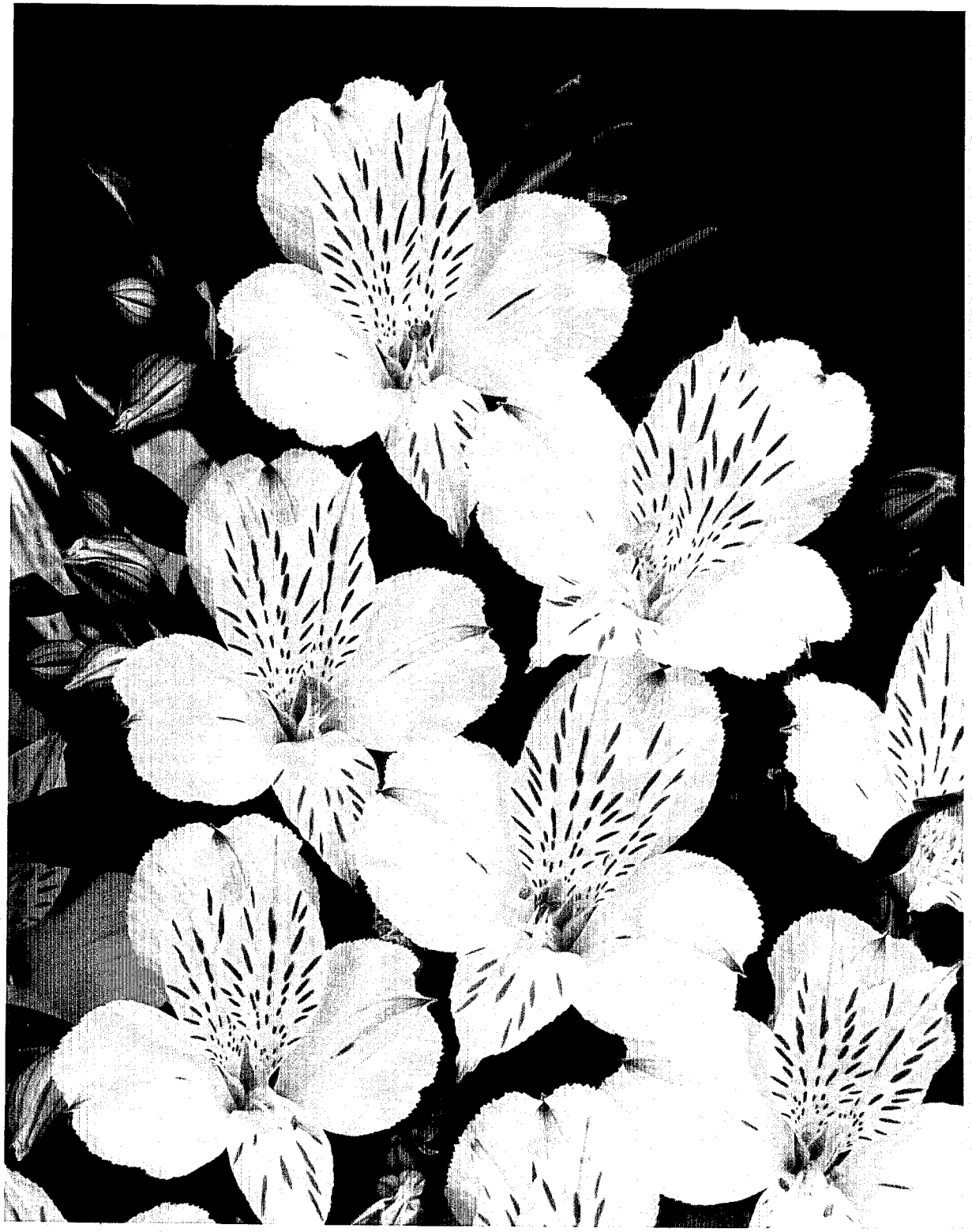

* * * * *